United States Patent [19]

Lapenskie

[11] Patent Number: 4,489,719
[45] Date of Patent: Dec. 25, 1984

[54] ANKLE SUPPORT

[76] Inventor: Garry P. Lapenskie, 148 Paperbirch Crescent, London, Ontario, Canada, N6G 1L7

[21] Appl. No.: 480,332

[22] Filed: Mar. 25, 1983

[51] Int. Cl.³ .............................................. A61F 13/06
[52] U.S. Cl. ................................ 128/80 H; 128/166; 36/89
[58] Field of Search ................ 128/166, 80 H, 166.5; 36/89; 273/55

[56] References Cited

U.S. PATENT DOCUMENTS

| | | | |
|---|---|---|---|
| 3,534,957 | 10/1970 | Norman et al. | 128/166 X |
| 3,613,273 | 10/1971 | Marquis | 36/89 |
| 4,392,487 | 7/1983 | Selner et al. | 128/166 X |
| 4,411,077 | 10/1983 | Slavitt | 128/80 H X |

Primary Examiner—John D. Yasko

[57] ABSTRACT

The present invention provides an ankle strap which can be attached to a shoe for mitigating ankle sprains. The strap comprises an elastic body portion having outer end regions, one of which is to be secured to the shoe optimally in a postero-inferior position to the base of the fifth metatarsal relative to the foot of the person wearing the shoe, and a releasable securing system for releasably securing the outer end regions to one another with the strap attached to the shoe and looped upon itself around the ankle.

5 Claims, 5 Drawing Figures

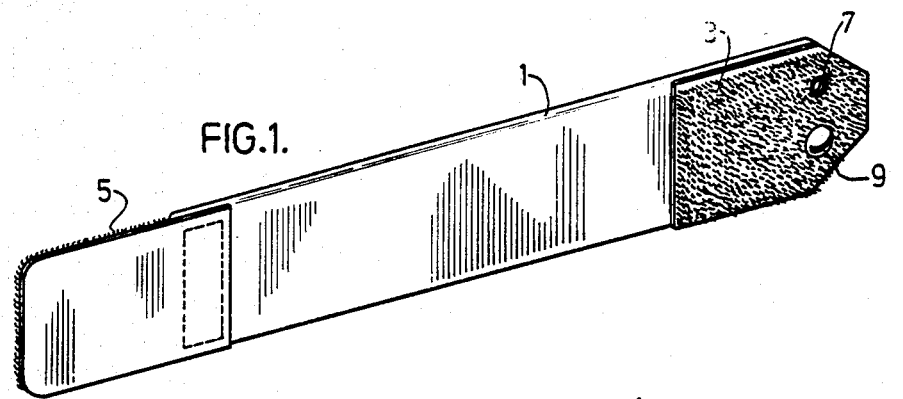
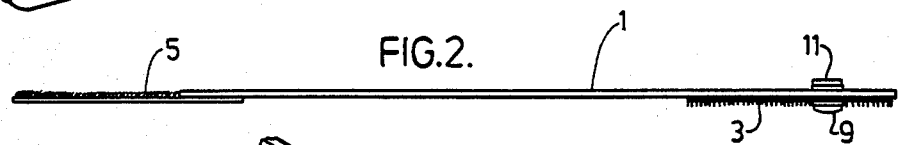
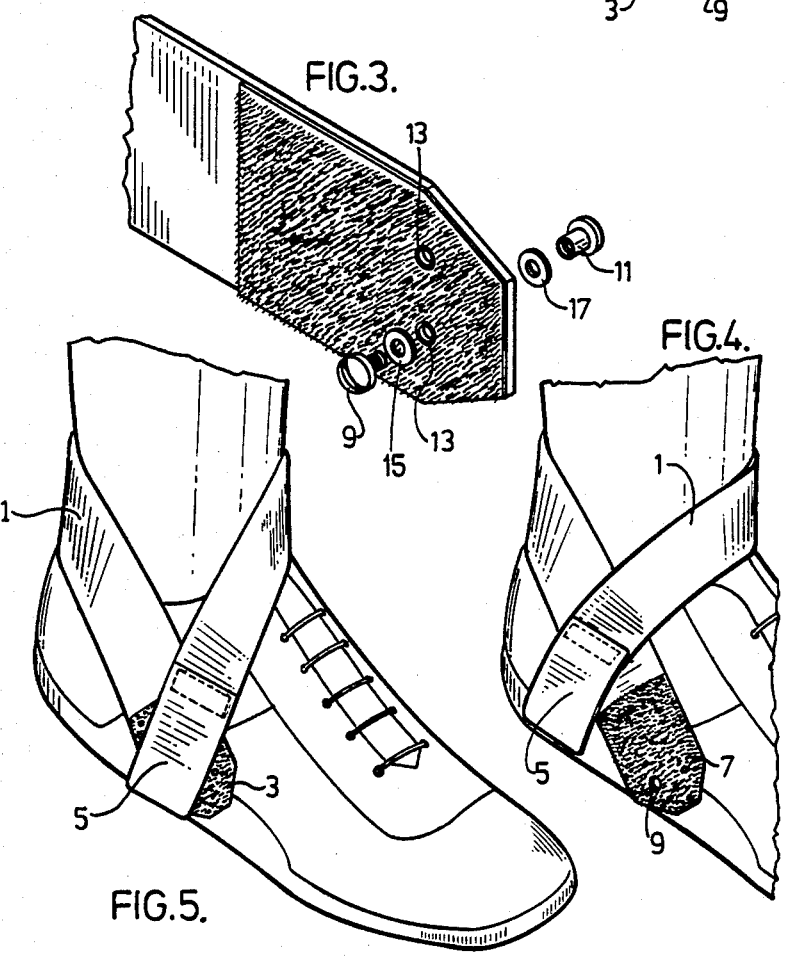

ANKLE SUPPORT

FIELD OF THE INVENTION

The present invention relates to an elasticized ankle strap which can be attached to a shoe for mitigating ankle sprains.

BACKGROUND OF THE INVENTION

As anyone who is involved in sports activities such as running and the like will appreciate, it is very easy to sprain an ankle as a result of a simple mis-step. For this reason, high cut running shoes have been developed for use in sports such as basketball; the high top running shoe provides in advance over the low cut running shoe but still suffers from lack of support problems since the shoe is still not tight around the ankle and permits ankle movement relative to the shoe. Furthermore, the added material in a high cut running shoe increases costs which are lost when any other part of the shoe wears out.

Many athletes have their ankles taped in preparation of a sporting event. The taping is initially effective but within a relatively short period loses its effectiveness as the tape is stretched and weakened with use of the ankle.

SUMMARY OF THE INVENTION

The present invention provides an ankle strap to be attached to a shoe for mitigating ankle sprains. The strap comprises an elastic body portion having outer end regions, one of which is optimally to be located in a postero-inferior position relative to the base of the fifth metatarsal of a foot of a person wearing the shoe and attached to the shoe in a manner so as not to interfere with the foot, and releasable securing means for releasably securing the outer end regions to one another with the strap attached to the shoe and looped upon itself around the ankle.

The elastic body portion of the strap adapts the strap to fit tightly to many different ankle sizes so that the strap is not limited to a particular size of ankle. Furthermore, according to preferred embodiments of the present invention the strap is attached to the shoe by releasable reusable attaching means which permits the strap to be reused regardless of the fact that the shoe itself may wear out and have to be replaced by a new shoe.

BRIEF DESCRIPTION OF THE DRAWINGS

The above as well as other advantages and features of the present invention will be described in greater detail according to the preferred embodiments of the present invention in which:

FIG. 1 is a perspective view looking down on an ankle strap arrangement according to a preferred embodiment of the present invention;

FIG. 2 is a plan view looking along an edge of the strap shown in FIG. 1;

FIG. 3 is an enlarged perspective view of the locating end of the strap shown in FIG. 1;

FIG. 4 is a perspective view of the strap attached to a shoe and wrapped around an ankle prior to securing the two strap ends to one another and FIG. 5 is a view similar to FIG. 4 with the strap ends releasably secured to one another.

BRIEF DESCRIPTION ACCORDING TO THE PREFERRED EMBODIMENTS

The ankle strap as best shown in FIGS. 1 and 2 comprises an elastic body portion 1 having a piece of hook Velcro 3 and a piece of loop Velcro 5 stitched to either end of the strap. It will be noted in these figures that the Velcro pieces are turned in opposite directions relative to one another on the strap.

The body of the strap is preferably about 12 inches in length, 2 inches in width and ⅛ inch in thickness. The piece of hook Velcro which is sewn directly to the strap is about 3 inches long and about 2 inches in width with the end of the strap at the hook Velcro being tapered to either side at about 1 inch from the end of the strap. With this taper the strap end is substantially flush with the bottom of the shoe regardless of wheter it is on the right or left shoe so that the strap end does not project below the shoe where it would otherwise be exposed to inadvertent pulling apart of the velcro fastener.

The loop Velcro is about 4 inches in length and again 2 inches in width and is overlapped by about 1 inch on the elastic strap so that the strap is free to stretch for an expanse of about 8 inches between the two pieces of Velcro.

At the hook Velcro end of the strap a pair of spaced apart holes are punched completely through the strap. These holes are used for locating and attaching the strap in proper position to a shoe.

The arrangement shown in the drawings further includes a reusable shoe attaching member in the form of a Chicago screw comprising a screw portion 9 and a barrel portion 11 for threadably receiving the screw portion.

The arrangement can be attached to virtually any type of shoe and is particularly useful on athletic footwear. The strap is attached to the shoe at a location where a specific part of the foot, namely the fifth metatarsal is positioned within the shoe. This location is one which maximizes the support provided by the strap when it is in a secured position around the ankle.

There are a number of different methods of attaching the strap. When working with canvas and leather shoes, a hole is punched through the shoe at the region directly behind the fifth metatarsal which is about one-third of the distance from the heel to the toes of the shoe. The ankle strap is then positioned with the hook Velcro facing out and the lower most of the two openings 7, which varies when the strap is used on the left or the right shoe, is aligned with the hole punched through the shoe. The barrel portion of the Chicago screw is then fitted from the inside of the shoe through the punched hole and the opening 7 in the strap and the screw portion is threaded into the barrel for releasably attaching the strap to the shoe. The strap itself is fitted with bushings 13 in each of the strap holes for strengthening of the material at these holes. Also provided are a pair of washers 15 and 17 to substantially prevent the screw from pulling through the strap. It should be noted that the head of the screw ball is flattened so as not to interfere with the foot of the user when the shoe is being worn.

As will be seen, the attached end of the strap is secured to the shoe near the tapered edge of the strap such that there is very little material below the attached region. This again reduces exposure of the strap of inadvertent catching and pulling of the strap from the shoe.

In the case of nylon shoes it is preferable to sew rather than to screw the strap to the shoe. However, for maximum support the strap is again optimally located in a poster-interior position relative to the base of the fifth metatarsal between the peronius brevis and the peronius longus which are the two muscles for controlling inward and outward sideways movement of the foot. As will be appreciated, the sewing method does not interfere with the foot inside the shoe.

In order to fasten the strap the shoe is first laced and the strap is pulled around the back of the leg about ¾ inch above the heel of the shoe and then around the inside of the leg over the top of the foot and looped upon itself such that the loop and hook Velcro engage with one another. It should be noted that in sewing the strap in place the strap is initially positioned where it sits at the proper height above the heel of the shoe so that the sewing allows the strap to be properly wrapped around the ankle. When the strap is attached to the shoe by the Chicago screw the screw allows the strap to be swung up into its proper position.

The strap as described above is designed to provide mechanical support for the ankle which substantially reduces ankle sprains. The mechanical support of the strap between the peronius brevis and the longus muscles offers resistance against the motion responsible for the majority of ankle sprains. It also provides support to weak ankles. In addition, since the ankle strap is mounted on the shoe coinciding with a specific landmark on the foot, personal idiosyncrasies in the foot structure are taken into account through the mounting technique. Furthermore, the main body of the strap is stretchable and the Velcro tabs are quite significant length to accommodate various different sizes of ankles.

As an added benefit of the present invention, regardless of whether the strap is screwed or sewn into position to the shoe, it is easily removed from the shoe so that it can be transferred from one pair of footwear to another.

Other methods of releasably securing the strap ends are also used with the strap, such as a hook and eye method where the elasticity of the strap maintains the hook within the eye. This arrangement is particularly useful when the strap is used with a soccer shoe or the like where the strap securing system comes into contact with wet and muddy conditions.

Although various preferred embodiments of the invention have been described herein and in detail, it will be apparent to those skilled in the art that variations may be made thereto without departing from the spirit of the invention or the scope of the appended claims.

The embodiments of the invention in which an exclusive property or privilege is claimed are defined as follows:

1. An ankle strap to be attached to a shoe for mitigating ankle sprains, said strap comprising an elastic body portion having outer end regions, an opening at one of said outer end regions to locate said one outer end region for attachment to the shoe in a postero-inferior position to the fifth metatarsal of a foot within the shoe, a Chicago screw for fitting through the opening and for attaching said strap to the shoe, said Chicago screw having a flattened head to avoid interfering with the foot and releasable securing means for releasably securing said outer end regions to one another with said strap attached to the shoe and looped upon itself around the ankle.

2. An ankle strap as claimed in claim 1 including a pair of spaced apart openings in said one outer end region for locating said strap to either a right or a left shoe.

3. An ankle strap as claimed in claim 1 wherein said elastic body portion spans about 8 inches between said outer end regions.

4. An ankle strap as claimed in claim 1 including a bushing in said opening.

5. An ankle support strap to be attached to a shoe, said strap comprising an elastic body portion having a first end adapted for attachment to the shoe, a second end free of the shoe and releasable securing means for releasably securing said first and second ends to one another with said strap attached to the shoe and looped upon itself around the ankle, said first end being tapered to either side for fitting with left or right shoes and having an aperture fitted with a bushing adjacent the taper to either side of the first end for receiving attaching means for attaching said strap to the shoe.

* * * * *